United States Patent [19]

Stile

[11] Patent Number: 5,067,503
[45] Date of Patent: Nov. 26, 1991

[54] DENTAL APPARATUS FOR FLOSSING TEETH

[76] Inventor: Thomas W. Stiles, 4858 Bryce Ave. E., Inver Grove Hts., Minn. 55075

[21] Appl. No.: 497,115
[22] Filed: Mar. 21, 1990
[51] Int. Cl.⁵ .............................................. A61C 15/00
[52] U.S. Cl. ................................... 132/324; 206/63.5; 132/323
[58] Field of Search ............... 132/309, 321, 322, 323, 132/324, 325, 326, 327, 328, 329; 206/63.5

[56] References Cited

U.S. PATENT DOCUMENTS

| | | | |
|---|---|---|---|
| 1,488,214 | 3/1924 | Mason | 132/324 |
| 1,792,429 | 2/1931 | Klinger | 132/309 |
| 2,981,264 | 6/1959 | DeFelice | 132/323 |
| 3,378,017 | 4/1968 | Stiles | 132/324 |
| 3,474,799 | 10/1969 | Cappello | 132/323 |
| 3,611,568 | 10/1971 | Alexander et al. | 30/45 |
| 3,631,869 | 1/1972 | Espinosa | 132/323 |
| 3,648,368 | 3/1972 | Douglass et al. | 30/60.5 |
| 3,772,779 | 11/1973 | Douglass et al. | 30/45 |
| 3,814,114 | 6/1974 | Roberts | 132/325 |
| 3,831,273 | 8/1974 | Wellinger | 30/43.92 |
| 3,850,182 | 11/1974 | Clark, Jr. | 132/309 |
| 3,892,249 | 7/1975 | Jones et al. | 132/323 |
| 3,939,853 | 2/1976 | Spanondis | 132/323 |
| 4,013,085 | 3/1977 | Wright | 132/323 |
| 4,139,940 | 2/1979 | Buras, Jr. et al. | 30/43.92 |
| 4,160,177 | 7/1979 | Ascoli | 310/22 |
| 4,162,687 | 7/1979 | Lorch | 132/323 |
| 4,192,330 | 3/1980 | Johnson | 132/323 |
| 4,253,477 | 3/1981 | Eichman | 132/323 |
| 4,655,233 | 4/1987 | Laughlin | 132/323 |
| 4,657,034 | 4/1987 | Koski | 132/324 |
| 4,753,254 | 6/1988 | McCullough et al. | 132/323 |
| 4,807,752 | 2/1989 | Chodorow | 132/323 |
| 4,827,952 | 5/1989 | Kos | 132/329 |
| 4,830,032 | 6/1989 | Jousson | 132/323 |
| 4,890,732 | 1/1990 | Shackelford | 132/309 |
| 4,941,488 | 7/1990 | Marxer et al. | 132/323 |

FOREIGN PATENT DOCUMENTS 2450603 11/1980 France .................................. 132/324

OTHER PUBLICATIONS

PCT/GB88/00254; 10-6-88; Neale et al. Improvements Relating to Dental Treatment.

Primary Examiner—Gene Mancene
Assistant Examiner—Adriene B. Lepiane
Attorney, Agent, or Firm—Palmatier & Sjoquist

[57] ABSTRACT

The present invention includes a housing having a plurality of individual sections of dental floss. Each of the floss sections includes a pair of balls in which opposite ends of the floss section are embedded. The balls are removably joined to the housing and mountable between extensions of a tooth brush-like hand tool which is manipulated during the flossing of teeth. The tool extensions are resiliently compressible together via angled face portions of the housing to be disposed between the balls. The tool extensions subsequently extend outwardly to engage the balls to remove the floss sections from the housings for flossing. After flossing, the floss sections are removed from the tool extensions by utilizing a container that includes angled face portions for drawing the extensions toward each other whereby the floss sections are released into the container for disposal.

22 Claims, 6 Drawing Sheets

DENTAL APPARATUS FOR FLOSSING TEETH

BACKGROUND OF THE INVENTION

1. Field of the Invention

The present invention relates to tools and floss for flossing teeth.

2. Description of the Prior Art

The prior art includes the Spandondis U.S. Pat. No. 3,939,853 issued Feb. 24, 1976. It discloses a scrubbing element with triangular end portions and a flosser head with bifurcated arms with recessed indentations. One may bias the spaced arms together to insert scrubbing element. The scrubbing element is provided with a raised pattern or texture.

The Mason U.S. Pat. No. 1,488,214 issued Mar. 25, 1924, discloses a combination toothbrush and dental floss holder with dental floss bridging between the arms of a U-shaped member. It also shows intersecting slots within which dental floss is frictionally held.

The Klinger U.S. Pat. No. 1,792,429 issued Feb. 10, 1931, discloses a dental floss holder with dental floss stretching between a pair of angularly disposed furcations. It includes a projection about which a free end of the floss may be wound.

The Roberts U.S. Pat. No. 3,814,114, issued June 4, 1974, discloses an apparatus for storing dental floss and for holding dental floss during use with a yoke for holding dental floss. It includes a cylindrical cassette from which dental floss is dispensed.

The Stiles U.S. Pat. No. 3,378,017 issued Apr. 16, 1968, teaches a dental floss applicator with dental floss being applied across two fork-like prongs. It includes a cylindrical handle member having an axial off-center bore therein for receiving a spool of dental floss.

The Clark U.S. Pat. No. 3,850,182, issued Nov. 26, 1974, is entitled *Dental Floss or Tape Holder for Use on a Toothbrush* and discloses a body with a pair of spaced arms made to support a strand of dental floss or tape. It includes binding knobs for anchoring the ends of a strand of dental floss.

The Koski U.S. Pat. No. 4,657,034, issued Apr. 14, 1987, teaches a dental floss dispenser.

SUMMARY OF THE INVENTION

A feature of the present invention is the provision in a dental floss apparatus having a hand tool with two spaced apart extensions for mounting a thread portion or section of dental floss, of tool connecting means affixed to opposing ends of the thread portion and being greater in width than the thread portion for connection to the tool extensions.

Another feature is the provision in such a dental apparatus, of a spacing means for disposing each of the tool connecting means in a spaced apart relation and in an accessible position for the extensions and wherein the spacing means includes a housing to which the tool connecting means is removably joined.

Another feature is the provision in such a dental apparatus, of the spacing means being in the form of a card with the tool connecting means disposed in openings and joined to interior card edges.

Another feature is the provision in such a dental apparatus, of the spacing means being in the form of a box-like housing and including a protuberance with a slit for disposing the thread portion in an accessible position on the exterior of the housing and wherein the thread portions are rotatably dispensed from the housing.

Another feature is the provision in such a dental apparatus, of a drawing means mounted on the housing for drawing the tool extensions toward each other so that the tool extensions may be disposed between the tool connecting means of the thread portion and wherein the tool extension means are subsequently extensible outwardly to cooperate with and remove the tool connecting means from the housing.

Another feature is the provision in such a dental apparatus, of drawing means being in the form of inwardly angled faces disposed on the housing and running downwardly toward the thread portions.

Another feature is the provisin in such a dental apparaus, of guide notches formed in the housing for guiding the tool extensions when the tool extensions are drawn together.

Another feature is the provision in such a dental apparatus, of disposing means being affixed to the housing for disposing of thread portions after flossing wherein the disposing means takes the form of a box-like container with a drawing or compressing means disposed near an opening formed in the container for drawing the tool extensions toward each other.

An advantage of the present invention is that dental floss is easily and quickly affixable to a dental floss tool.

Another advantage is that the dental floss section or thread portion is quickly and easily removable from the dental floss tool into a convenient disposing means.

Another advantage is that the thread portions are not touched by fingers or hands and hence remain extremely sanitary for flossing.

Another advantage is that thread portions are mounted tightly and securely on a dental floss tool.

Another advantage is that the card mounting the plurality of dental floss sections is compact yet mounts one-half month's supply of dental floss. Furthermore, a card depleted of dental floss sections is replaceable in the housing with a card having a full supply of floss sections.

Another advantage is that dental floss is conserved as no wrapping or tying operations are required.

Other advantages are that the dental apparatus is easy to fabricate, inexpensive and simple to operate.

DESCRIPTION OF THE PREFERRED EMBODIMENT

Figure 1:
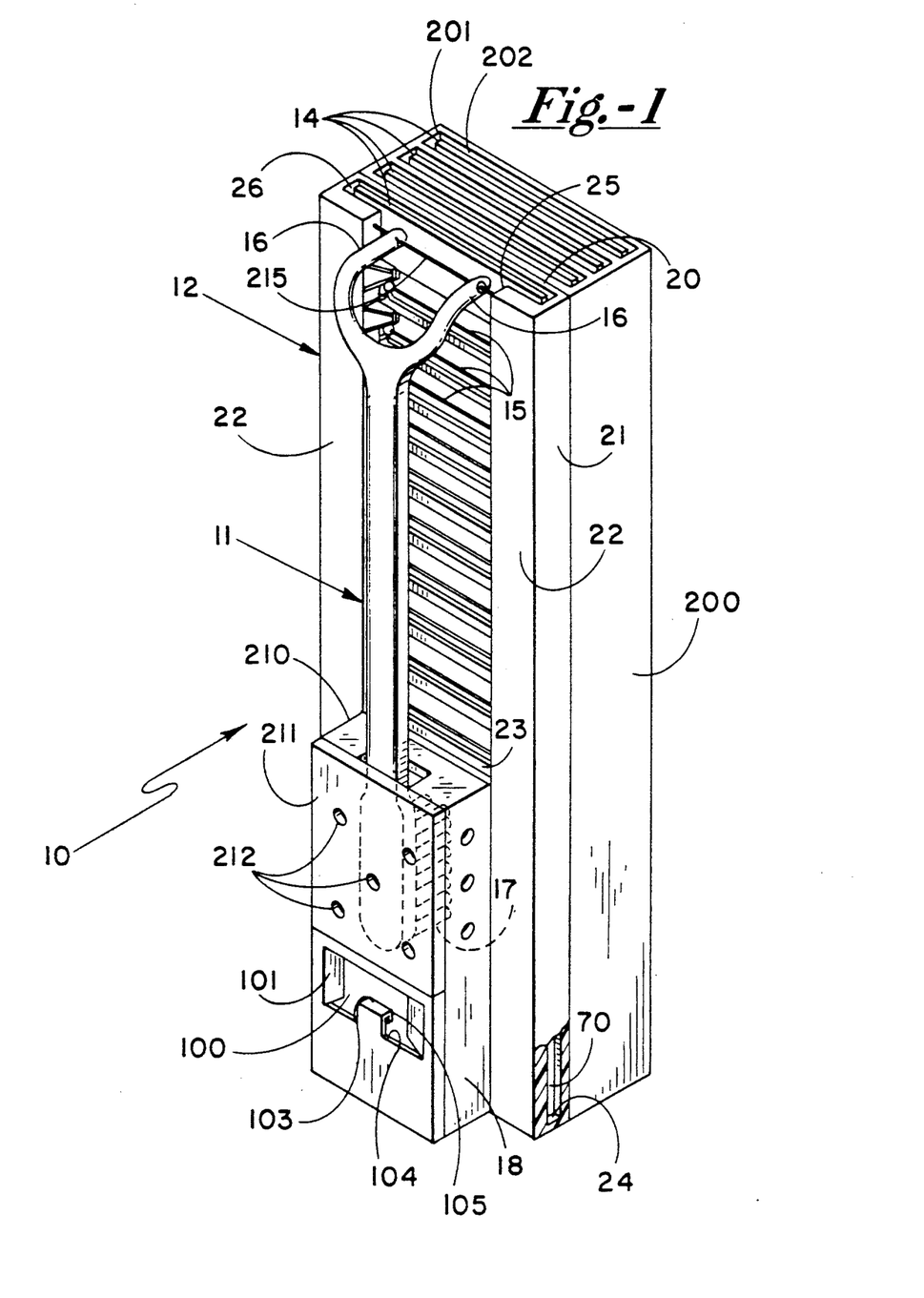
FIG. 1 is a perspective view of the dental apparatus including the dental flossing tool and floss cassette.

As shown in FIG. 1, the dental apparatus is indicated in general by the reference numeral 10 and includes a flosser or flossing hand tool 11, a housing 12 with a plurality of cams or angled guides 13 and a slidable floss card 14 with a plurality of floss sections 15. One end of the flosser 11 includes a pair of extensions 16 for mounting one of the floss sections 15. The other end of the flosser 11 includes bristles 17 such as in a conventional toothbrush. A disposing means 18 is affixed to the housing 12 for disposing of used floss sections 15.

The housing 12 includes an elongate back panel 20 integrally connected to side panels 21 which in turn are integrally connected to front panels 22. Front panels 22 are integrally connected to each other by a bottom front panel 23. A floor panel 24 is integrally connected to the panels 20, 21, 22 and 23. The interior edges of front panel 22 and the upper edge of bottom front panel 23 form an opening 25 which allows access to the floss sections 15 by the flosser extension 16. Each of the front panels 22 and the back panel 20 form respective slots 26 for receiving the card 14.

Figure 2:
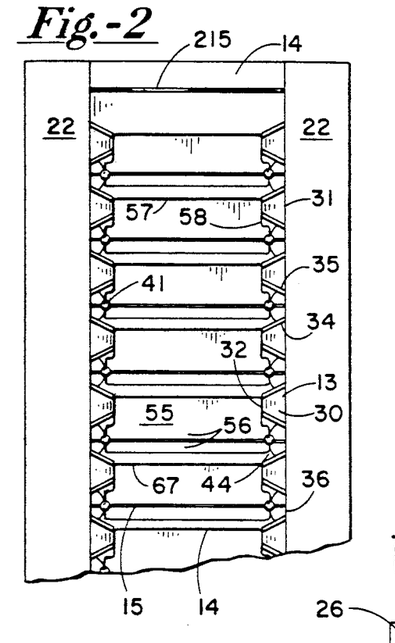
FIG. 2 is partial, side elevation, detail view of the floss cassette of FIG. 1.
Figure 3:
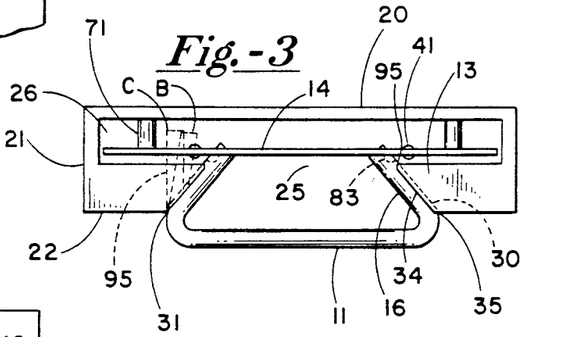
FIG. 3 is an end, detail view of the floss cassette of FIG. 1.
Figure 5:
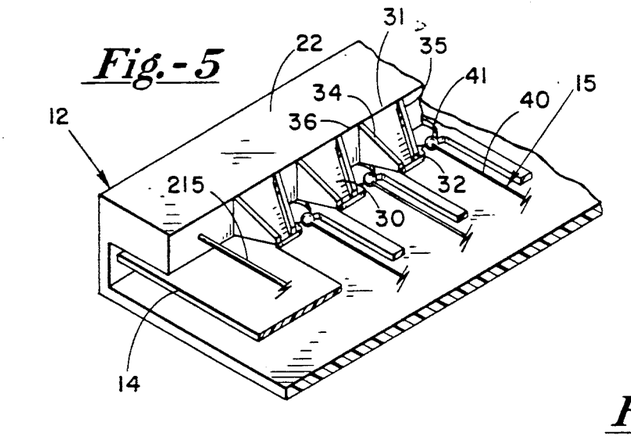
FIG. 5 is a perspective, detail, partial view of the cassette and card of FIG. 1.

As shown in FIGS. 2, 3 and 5, each of the cams 13 of the housing 12 includes an angled, converging glide surface 30 extending inwardly and toward the card 14 from an upper outer wider edge 31 to a lower inner narrower edge 32. Each of the cams 13 further includes a pair of respective upper and lower guide ridges 34, 35 converging toward each other for guiding and bearing against the extension 16. Housing 12 further includes edge portions 36 disposed substantially in line with upper cam edges 31.

Figure 4:
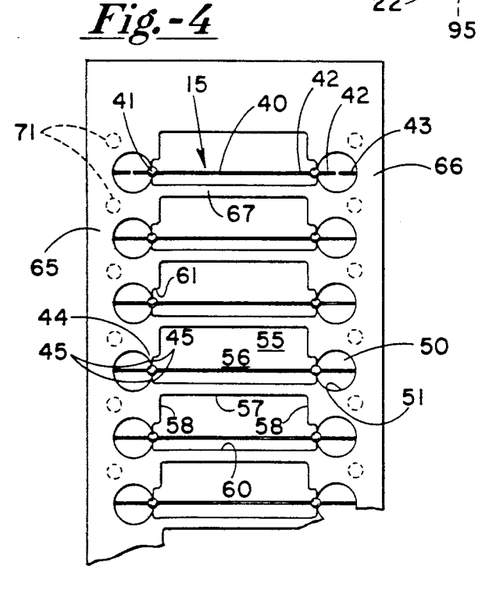
FIG. 4 is a side elevation, detail view of the floss section card of the cassette of FIG. 1.

As shown in FIG. 4, each of the floss sections 15 of the card 14 includes a thread section or thread portion or piece of floss 40 affixed between a pair of balls or tool connecting means 41. End thread portions 42 are embedded in the balls 41 and are shown severed from excess pieces of floss 43 utilized in the fabrication process. The balls 41 are affixed to the card 14 via a pair of tips 44 extending from interior curved card edges 45.

The card 14 further includes a plurality of circular holes 50 formed by interior curved card edges 51 and curved edges 45. Each of the holes 50 receives approximately a one-half portion of its respective ball 41.

Card 14 further includes a plurality of tool receiving openings 55, and a plurality of thread receiving openings 56. Each of the openings 55 communicates with its respective opening 56. Each of the openings 55 is formed by an upper interior card edge 57 and side interior card edges 58. Each of the openings 56 is formed by a bottom interior card edge 60, curved edges 45 of tips 44, balls 41, and linear edge portions 61. Opposing side portions 65, 66 of the card 14 are supported relative each other by integral lateral support bars 67.

The card 14 further includes a bottom portion 70 disposed transversely of the disposing means 18 in panel 23. The bottom portion 70 may lack openings 55, 56 holes 50, and floss sections 15. The card 14 also includes a plurality of integral rod-like nubs 71 extending from each of the side portions 65, 66 to dispose the card 14 in the slot 26 with a minimum of movement between the back panel 20 and front panels 22. The width of the card 14 is approximately equal to the spacing between the inner dimensions of the side panels 21 to minimize lateral movement.

One of the purposes of the card 14 is to dispose the floss sections 15 in a spaced apart relation from each other for access by the tool 11. Another purpose is to space the balls 41 of a particular floss section 15 apart from each other so that the thread section 40 is held linearly but with a slight amount of slack so as to prevent a splitting of the floss portion or thread section 40 or to preclude the thread section 40 from being loosened relative to its respective balls 41.

It should be noted that the tips 44 and balls 41 are integrally connected. The card 14 and balls 41 are typically molded over the thread sections 40 with the waste floss portions 43 being severed from the end floss portions 42 after the molding process.

As shown in FIGS. 2 and 4 the effective lateral distance between the upper and lower cam edges 31, 32 of each of the cams 13 is only slightly longer than the diameter of each of the balls 41 so that the extensions 16 of the tool 11 are compressed minimally. Each of the inner edges 32 is aligned with its respective interior edge 58. Each of the inner portions of each of the upper guide walls 34 leads into its respective upper interior card edge 58. Edge portions 36 are aligned with upper cam edges 31 and are spaced outwardly of the balls 41 so that the balls 41 are readily removed from the card 14 and housing 12. Adjacent guide walls 34, 35 of adjacent cams 13 are spaced to allow a visual observation of the connection between the tips 44 and the balls 42.

Figure 6:
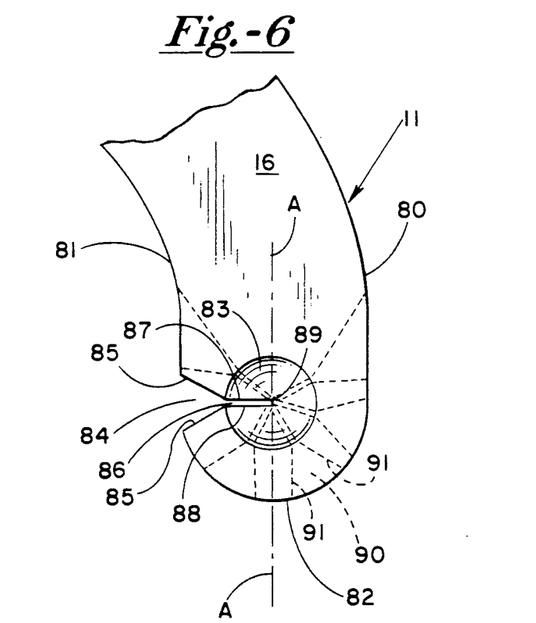
FIG. 6 is a detail partial view of the flossing tool of FIG. 1.
Figure 7:
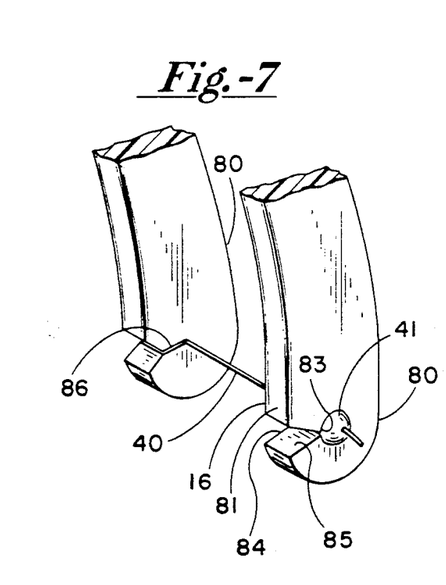
FIG. 7 is a detail partial view of the flossing tool of FIG. 1 engaging a section of floss.

Each of the extensions 16 of the flosser 11 includes an upper edge 80 and a lower edge 81 which lead into each other at a distal point 82. A socket 83 for receiving the ball 41 is disposed equidistant between the edges 80, 81 and distal point 82. The socket 83 is spherical and receives approximately one-half of the ball 41. A floss guide slot 84 is formed in lower edge 81 by converging edge portions 85. Edge portions 85 lead into a floss slit 86 formed by respective upper and lower interior parallel faces 87, 88. Slit 86 includes an end portion 89 disposed centrally in the socket 83.

Figure 8:
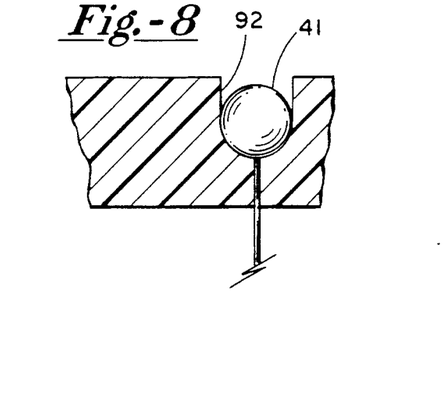
FIG. 8 is a detail partial view showing an alternate embodiment of the dental flossing tool having a deeper socket for receiving the ball of the dental floss section.

The converging edge portions 85 guide the thread portion 40 into the slit 86. The slot 84 and slit 86 are disposed perpendicular to flossing pressure points indicated by line A. During flossing, the thread section 40 typically bears alternately on upper and lower faces 87, 88 of end slot portion 89 and the extensions are manipulated up and down between teeth along line A. Pressure typically is not brought to bear on a line normal to line A and, accordingly, the positioning and removal slit 86 is formed on such a perpendicular line to minimize unintended removal of the floss section 15 during flossing. Alternate guide slots to slot 84 are indicated by the reference numeral 90 and phantom lines 91 which define converging edge portions. An alternate socket to socket 83 is indicated by reference numeral 92. Socket 92 is deeper than socket 83 and receives the entire ball 41. Socket 92 may provide a more secure receptacle for the floss section 15 when flossing pressures are brought to bear on lines perpendicular to line A as a greater surface area of the ball 41 may bear against the spherical wall portions forming the socket 92 and as the ball 41 is less likely to pop out of the deeper socket 92.

Extensions 16 are resilient and spaced so that the distance between opposing outer faces 95 of the extensions 16 are approximately equal to the distance between opposing upper cam edges 31. The extensions 16 are also sufficiently spaced so as to drawn the thread section 40 tautly for the purpose of flossing. The distance between linear portions of edges 80, 81 of the extension 16 is typically less than the length of each of the upper cam edges 31 to allow the extension 16 to slide easily into the cams 13. The distance between linear edge portions 80, 81 of the extension 16 is typically slightly less than or approximately equal to the distance between linear edge portions 60, 61.

The disposal container means 18 for disposing of used dental floss sections 15 is box-like and includes an opening 100. A pair of cams 101 form side edges of the opening 100 and converge inwardly and toward each other for compressing for drawing the extensions 16 together and loosening a used floss or thread section 15. A U-shaped removal stem 103 is affixed to a bottom edge 104 and includes a downwardly extending arm 105.

In operation, to connect a floss section 15 to the flosser 11, the card 14 is slid into the slot 26 until the bottom edge of the bottom portion 70 bears against the floor 24 of the housing 12. In such a position, the openings 55 are aligned with the cams 13, with each of the upper edges 57 leading into their respective cam guide walls 34, and lower cam edges 32 are aligned with interior card edges 58. Subsequently, the distal points 82 of the tool extensions 16 are brought to bear on the cam surfaces 30 and an inward pressure is exerted on the tool 11 so that the extensions 16 are drawn or resiliently compressed together as they slide on the cam surfaces 30. The guide walls 34, 35 may bear against the extensions 16 which are accordingly guided into opening 55. After the extensions 16 have been inserted sufficiently into the opening 55 so that the sockets 83 are disposed in the same plane as the card 14, the tool is manipulated toward the disposal means 18 and extensions 16 are slid into openings 56 so that the thread section 40 is received through the guide slot 84 and into the end portion 89 of the slit 86. As the extensions 16 begin to move into the openings 56, the extensions 16 slide over the ridges 34. As the extensions 16 slide more fully into the openings 56 so that the thread section 40 is received into end portion 89, the extensions 16 resiliently snap away from each other as they slide off of interior card edges 58. As the extensions 16 resiliently snap apart, the balls 41 are received in the sockets 83 and the extensions 16 are lifted from the card 14 so as to disconnect the balls 41 from their respective tips 44. When the balls 41 are disconnected, the extensions 16 are resiliently drawn further apart to approximately the position shown by B in FIG. 3 so as to draw the thread section 40 sufficiently taught for flossing purposes.

During flossing, pressure is typically exerted on the thread section 40 along line A, especially if the spaces between teeth being flossed are relatively narrow. If pressure perpendicular to line A is exerted on the floss section 40, the floss section 40 may be drawn partially into slit 86, but the balls 41 typically maintain the thread section 40 between the extensions 16 by bearing against the spherical wall portions of the socket 83. If thread section 40 splits or is loosened by flossing, the resilient extensions 16 simultaneously and immediately draw the balls 41 apart so as to draw the thread section 40 tight. If the resilient extensions 16 are drawn to the fully decompressed position as shown by letter C, then the connected thread section 40 may be disposed of in the disposing means 18 and a new thread section 40 may be readily connected from the card 14.

After flossing, floss section 15 may be disposed of in the disposal means 18 by inserting the extensions 16 into the opening 100 and against the cams 101. The extensions 16 are thus drawn together so as to loosen the thread portion 40. The thread portion 40 may be manipulated under and into the U-shaped stem 103 and the thread section 40 may be brought to bear on arm 104 to slip the section 15 from the extensions 16.

Figure 9:
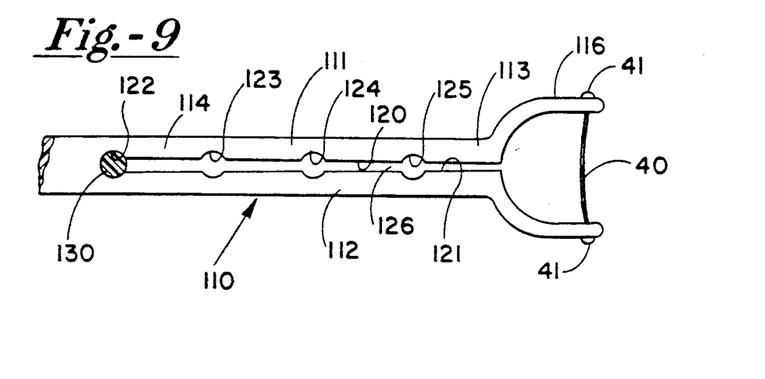
FIG. 9 is a partial top plan view of an alternate flossing tool.

As shown in FIG. 9, an alternate flossing tool 110 includes a pair of side portions 111, 112. Each of the side portions 111, 112 includes a front end 113 and a rear end 114. Each of the side portions 111, 112 converge and taper rearwardly from its front end 113 to its rear end 114. Each of the front end 113 is typically connected to its respective tool extensions 116. Each of the tool extensions is shaped like its corresponding extensions 16 of the flosser 11 and includes like sockets.

Extensions 111, 112 include respective inner edges 120, 121 which extend frontwardly and inwardly toward each other. Each of the edges 120, 121 includes a set of four opposing curved recesses 122, 123, 124 and 125. When the side portions 111, 112 are in an unbiased position as shown in FIG. 9, recesses 122 are spaced at a greater distance than are respective recesses 123, 124 and 125. Likewise recesses 123 are spaced at a greater distance from each other than are recesses 124 and 125; and recesses 124 are spaced at a greater distance from each other than are recesses 125. Edges 120, 121 and slots 122-125 form a peg-receiving slot 126.

Figure 10:
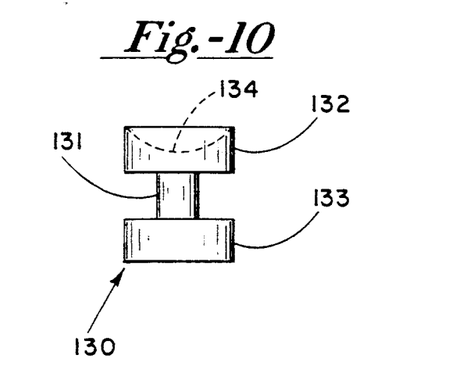
FIG. 10 is a side elevation view of one type of peg for the flossing tool of FIG. 9.
Figure 11:
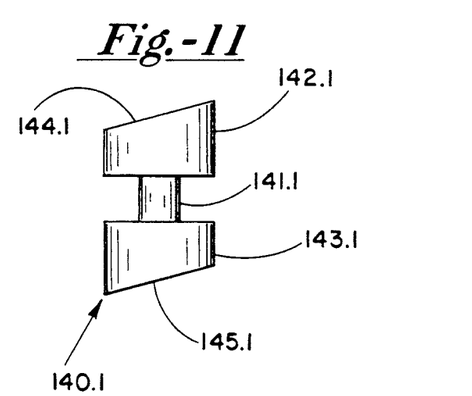
FIG. 11 is a side elevation view of another peg for the flossing tool of FIG. 9.

A key or peg 130 is slidable in the slot 126. The peg 130 includes a cylindrical pin 131 with upper and lower disc-like knobs 132, 133 integrally connected to the pin 131. Upper knob 132 has a concave depression 134 formed therein for receiving a finger or thumb. An alternate key or peg 140.1 includes a cylindrical pin 141.1 and upper and lower integral rounded knobs 142.1, 143.1. The knobs 142.1, 143.1, 143 have respective planar angle faces 144.1, 145.1 running generally parallel to each other. The angle faces 144.7, 145.1 form finger or thumb stops for sliding the peg 140.1 back and forth in slot 136 therein.

When the flosser 110 is an unbiased position, the peg 130 is received in recesses 122. The distance between the recesses 122 is approximately the same as the diameter of the pin 131. The distance between the interior faces of the knobs 132, 133 is approximately equal to the thickness of the flosser 110 so that the peg 130 slides through the slot 126 with some friction between the inner faces of the knobs 132, 133 and the upper and lower faces of the flosser side portions 111, 112.

As the peg 130 slides from recess 122 to recess 123, the side portions 111, 112 and extensions 116 are drawn apart to tighten the floss section 40 for flossing. If the floss section 40 is loosened during flossing, the peg 130 is moved up a notch to recesses 124 to further draw apart the side portions 111, 112 and extensions 116 to further tighten the floss section 40. Extensions 116 may be further drawn apart and the floss section 40 further tightened by sliding the peg 130 up still another notch to recesses 125. It should be noted that extensions 116 are resilient as are the extensions 16 in flosser 11.

Figure 12:
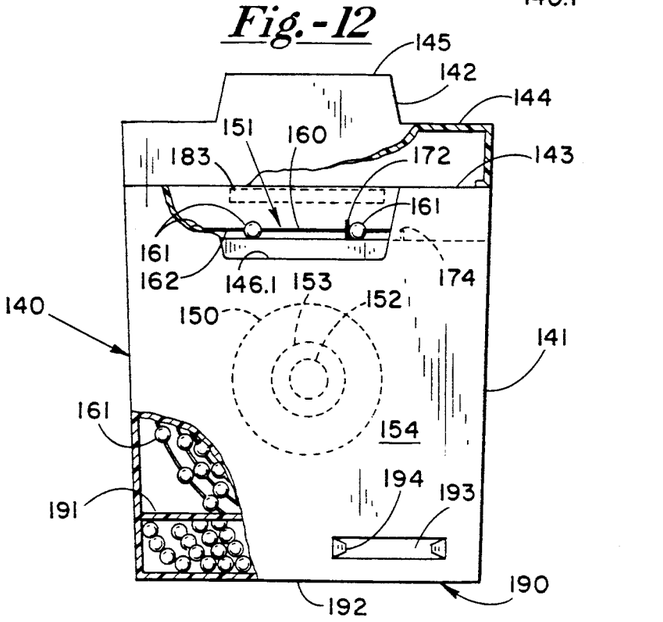
FIG. 12 is a side elevation view of an alternate embodiment of the dental floss apparatus.
Figures 13, 14, 15:
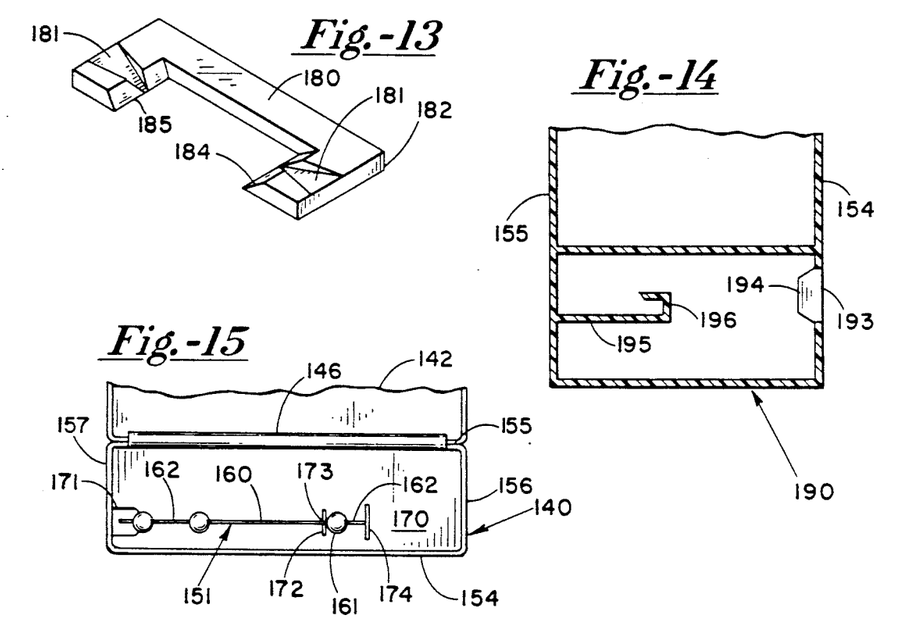
FIG. 13 is a perspective fragmentary view of a cam for the embodiment in FIG. 12.
FIG. 14 is a partial cut away view of the embodiment of FIG. 12 showing a disposing means for the used floss sections.
FIG. 15 is a top plan view of the opened embodiment of FIG. 12.

Alternate dental apparatus 140 includes a box-like housing 141 with a lid 142. A top edge 143 of the housing 140 cooperates with a lip 144 of the lid 142. The lid 142 includes an extension 145 which is formed to fit a U-shaped opening 146.1 in the housing 141. A hinge 146 connects the lid 142 to the housing 140. A spool or rotatable means 150 for holding a plurality of thread sections 151 is affixed in the housing 141. Spool 150 is rotatable affixed via an integral axle 152 mounted in a pair of bearings 153. Each of the bearings 153 is affixed to interior faces of the front and rear panels 154, 155 of the housing 141. The housing 141 further includes side panels 156, 157. Each of the floss sections 151 includes a thread section 160 and two balls 161 in which the ends of the thread section 160 are embedded. Each of the floss sections 151 is joined by a cuttable thread portion 162.

An upper edge 170 is affixed between the panels 154-157 and includes an opening 171 for the floss sections 151 and their respective balls 161. A protuberance 172 extends upwardly from the edge 170 and includes a slit 173 having a width approximately the width of the thread section 160 and narrower than each of the balls 161. A blade 174 with a cutting edge for cutting thread portions 162 is disposed opposite the opening 171 and is approximately one-half the length of the thread portion 162 from protuberance 172. The height of the blade 174 is typically less than the height of the protuberance 172.

A cam or drawing means 180 may be affixed to the rear panel 155 if flosser 11 is desired to be utilized. The cam 180 includes a pair of camming grooves 181 which function similar to cams 13 to draw in extensions 16 of flosser 11. The cam 180 includes a rear edge 182 which may be affixed to a face portion 183 of the rear panel 155 to be disposed over the protuberance 172 so that an edge 184 of one of the camming grooves 181 is directly above the protuberance 172, and another edge 185 of the other cam and groove 181 is directly above the inner point of the non-joined ball 161 paired with the ball 161 joined adjacent to the protuberance 172.

The housing 141 further includes disposing means 190 formed by upper and lower floor panels 191, 192 front and rear panels 154, 155 and side panels 156, 157. The disposing means 190 includes an opening 193 formed in front panel 154 partially formed by a pair of cams or drawings means 184 for drawing in extensions 16 in a flosser 11. A stem 195 with an arm 196 is connected to rear panel 155 and disposed opposite opening 193.

Figure 16:
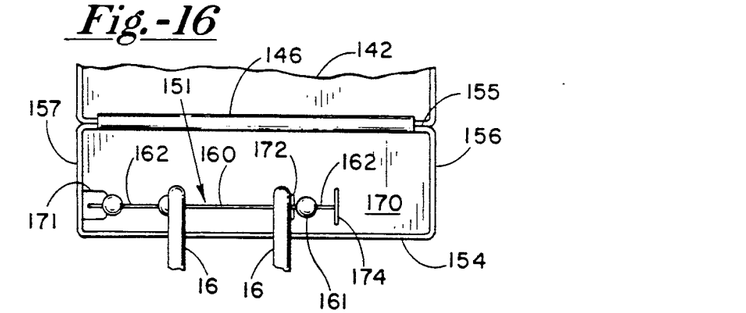
FIG. 16 is a top plan view of the opened embodiment of FIG. 12 with one of the flossing tools.
Figure 17:
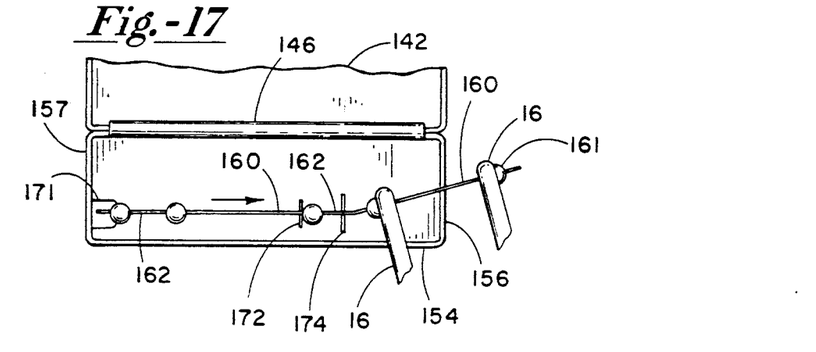
FIG. 17 is a top plan view of the opened embodiment of FIG. 12 and shows one of the flossing tools being manipulated to cut a dental floss section.

In operation, flossing tool 110 (or flosser 11) in an unbiased position with peg 130 between recesses 122 is disposed over the floss section 151 and manipulated so that the thread portion 160 is received in slits 86. The flosser 110 is lifted to draw the thread section 160 out of the slit 173 of protuberance 172. Subsequently, the peg 130 is slid into recesses 123 to draw the thread section 160 tightly and draw the balls 161 into the sockets 83. The flosser 110 is then manipulated so that the immediately succeeding thread portion 160 is slid into the slit 173 of the protuberance 172. After the immediately succeeding thread portion 160 has been received in the slit 173, the thread portion 162 is severed by the cutting edge of the blade 174 so as to free the first floss section 151 for flossing. After flossing, the floss section 151 is disposed of in the disposing means 190 utilizing the cams 194 to bear against and draw in extensions 116 with stem 196 picking off the floss section 151 via the thread section 160.

It should be noted that either of the flossing tools 11 or 110 may be utilized with either of the embodiments 10 or 140.

It should be further noted that a storage container 200 may be affixed to the back panel 20 of the housing 12. The container 200 includes a set of dividers 201 that form a set of slots 202. Each of the slots 202 receives for storage a floss card 14.

It should further be noted that the toothbrush bristles 17 may be received in a sanitary box 210. The box 210 includes a cover 211 resiliently biased toward a closed position. The box 210 includes a plurality of air holes 212 to allow air circulation in the box 210.

Furthermore, the housing 12 may include a wire or floss like tool storage hanger 215 affixed between front panels 22. When not in use, the tool 11 may be hung via its slots 84 or slits 86 on the wire hanger 215.

Figure 18:
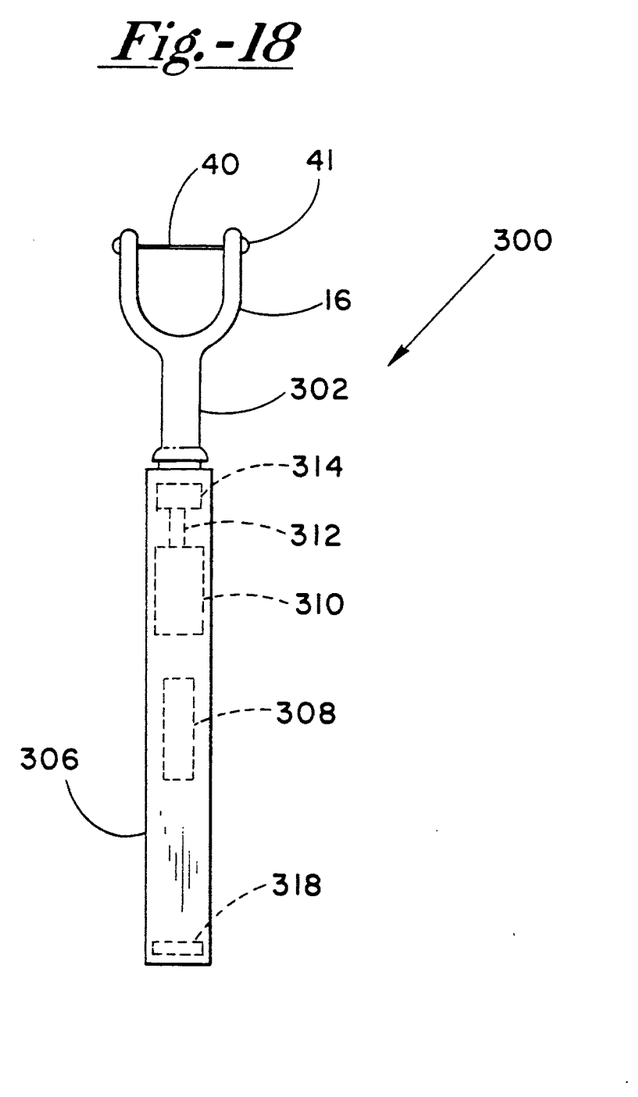
FIG. 18 is an elevation, partially schematic view of an alternate embodiment of the dental apparatus.

In an alternate embodiment as shown in FIG. 18, a vibrating flossing tool 300 includes a head portion 302 which is integrally connected to the pair of floss-mounting tool extensions 16 having thread section 40 and balls 41. The head portion 302 is connected to one end of a tubular handle member 306 which houses a vibration-including means described below. With respect to the vibration-inducing means, the Douglass et al. U.S. Pat. No. 3,772,779 issued Nov. 20, 1973, the Douglass et al. U.S. Pat. No. 3,648,368 issued Mar. 14, 1972, and the Alexander et al. U.S. Pat. No. 3,611,568 issued Aug. 20, 1969 are hereby incorporated by reference.

The handle 306 includes a battery 308 and an electric motor 310. Extending from the motor. 310 in the direction of the head portion 302 is a rotatable shaft 312 on which is mounted an eccentric or unbalanced weight 314. The weight is mounted eccentrically on the shaft 312 so that the center of gravity of the weight is removed from the axis of rotation of the weight. The handle 306 also includes a switch 318.

In operation, the switch 318 is turned on and electrical energy from the battery 308 is directed to the motor 310. Energization of the motor 310 causes rotation of the shaft 312 and thereby rotation of the eccentrically or unbalanced weight 314. The eccentricity of the weight mounting, i.e., the displacement of the center of gravity of the weight from the axis of rotation of the weight, and the disposition of the weight proximate the head portion 302 induces vibration of the head portion 302 and therefore of the extension 41. Such vibration imparts a back and forth or slicing motion to the floss 40 whereby the floss 40 readily slides between teeth to floss and stimulate the gums.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

I claim:
1. A dental apparatus for manipulating dental floss comprising:
    (a) a hand tool with a handle and two spaced apart extensions,

(b) a thread section for flossing teeth and having two end portions, (c) tool connecting means affixed to each of the end portions of the thread section for connecting the thread section between the extensions of the tool, the tool connecting means being greater in width than the thread section, (d) housing means for movably engaging a plurality of tool connecting means and accompanying thread sections such that the tool connecting mean are accessible for the tool extensions, and (e) discarding means including storage means on the housing means for engaging a plurality of tool connecting means for discarding and storing the thread sections.

2. The dental apparatus of claim 1, wherein the tool connecting means comprises a pair of balls, each of the balls being connected to one of the thread end portions.

3. The dental apparatus of claim 2, wherein each of the extensions of the hand tool includes a socket for receiving one of the balls and a slit for receiving the thread section.

4. The dental apparatus of claim 3, wherein the depth of each of the sockets is greater than the diameter of its respective ball.

5. The dental apparatus of claim 1 wherein the hand tool includes vibration means for vibrating the spaced apart extensions and the thread section.

6. The dental apparatus of claim 1, wherein the discarding means includes an opening, and further including a stem disposed transversely of the opening for removing the thread section from the tool.

7. The dental apparatus of claim 6, wherein the discarding means includes drawing means forming a portion of the opening for drawing the tool extensions inwardly for removing the thread section from the tool.

8. A dental apparatus for manipulating dental floss comprising:

(a) a hand tool with a handle and two spaced apart extensions, (b) a third section for flossing teeth and having two end portions, (c) tool connecting means affixed to each of the end portions for connecting the thread section between the extensions of the tool, the tool connecting means being greater in width than the thread section, and (d) spacing means for disposing each of the tool connecting means in a spaced apart relation and in an accessible position for the extensions, the tool connecting means being removably joined to the spacing means so that the tool connecting means and thread section are removable from the spacing means for the flossing of teeth, the spacing means including a card with a pair of opposing guide edges and a pair of connection edges, one of the tool connecting means being integrally affixed to each of the connection edges, each of the guide edges leading into one of the connection edges, the distance between the guide edges being less than the distance between the tool extensions, the distance between the connection edges being less than the distance between the tool extensions and greater than the distance between the guide edges such that the tool extensions snap outwardly from the guide edges to the tool connecting means.

9. The dental apparatus of claim 8, wherein the tool connecting means includes balls in which the thread end portions are embedded, and each of the extensions including a socket for receiving one of the balls and a slit for receiving the thread section.

10. The dental apparatus of claim 9, wherein the depth of each of the sockets is greater than the diameter of its respective ball.

11. A dental apparatus for manipulating dental floss comprising:

(a) a hand tool with a handle and two spaced apart extensions, (b) a thread section for flossing teeth and having two end portions, (c) tool connecting mean affixed to each of the end portions for connecting the thread section between the extensions of the tool, the tool connecting means being greater in width than the thread section, (d) spacing means for disposing each of the tool connecting means in a spaced apart relation and in an accessible position for the extensions, the tool connecting means being removably joined to the spacing means, and (e) drawing means engagable with the spacing means for drawing the tool extensions toward each other and between the tool connecting means for cooperating with the tool connecting means, the drawing means including a pair of spaced apart side members, each of the side members comprising an angled face converging toward the angled face of the other side member and defining a plane of convergence, the plane of convergence being offset relative to the thread section such that the tool extensions move out of the plane of convergence to engage the thread section whereby the thread section and tool connecting means are removable from the spacing means for the flossing of teeth.

12. The dental apparatus of claim 11, wherein each of the faces includes a pair of ridges for guiding the extensions.

13. The dental apparatus of claim 11, wherein the spacing means includes a card with an opening formed therein by interior card edges, the tool connecting means being joined to portions of the interior card edges, the card being slidable into the drawing means.

14. The dental apparatus of claim 13, wherein the interior card edges include edge sections disposed inwardly of the interior card edge portions and the tool connecting means, the drawing means leading into the edge sections, the edge sections leading into the interior card edge portions so that the extensions are drawable between the tool connecting means and resiliently snappable outwardly to engage the tool connecting means.

15. The dental apparatus of claim 11, wherein the tool connecting means comprises a pair of balls, and each of the extensions including a socket for receiving one of the balls, and a slit for receiving the thread section.

16. The dental apparatus of claim 15, wherein the depth of each of the sockets is greater than the diameter of its respective ball.

17. A dental apparatus for manipulating dental floss comprising (a) a hand tool with a handle and two spaced apart extensions, (b) a thread section for flossing teeth and having two end portions, (c) tool connecting means affixed to each of the end portions for connecting the thread section between the extensions of the tool, the tool connecting means being greater in width than the thread section, (d) spacing means for disposing each of the tool connecting means in a spaced apart relation and in an accessible position for the extensions, the tool connecting means being removably joined to the spacing means so that the tool connecting means and thread section are removable from the spacing means for the flossing of teeth, and (e) discarding means including storage means engagable with the spacing means for removing the thread section from the tool for discarding and storing the thread section.

18. The dental apparatus of claim 17, wherein the spacing means includes a protuberance with a slit, the slit being lesser in width than the tool connecting means and greater in width than the thread section whereby the tool connecting mean and thread section are removably joined to the protuberance.

19. The dental apparatus of claim 18 and including a plurality of thread sections and tool connecting means mounted on a rotatable means affixed to the spacing means, and further including cuttable thread portions joining successive thread sections and corresponding tool connecting means, and a blade with a cutting edge disposed transversely of the protuberance for cutting the thread portions.

20. The dental apparatus of claim 18, and further including drawing means mounted over the protuberance for drawing the tool extensions toward each other and between the tool connecting means.

21. The dental apparatus of claim 17, wherein the discarding means includes an opening, and further including a stem disposed transversely of the opening for removing the thread section from the tool.

22. The dental apparatus of claim 21, wherein the discarding means includes drawing means forming a portion of the opening for drawing the tool extensions inwardly for removing the thread section from the tool.

* * * * *

UNITED STATES PATENT AND TRADEMARK OFFICE
CERTIFICATE OF CORRECTION

PATENT NO. : 5,067,503

DATED : November 26, 1991

INVENTOR(S) : Thomas W. Stiles

It is certified that error appears in the above-identified patent and that said Letters Patent is hereby corrected as shown below:

On the title page, item [75] Inventor: "Stiles" should read --Stiles--.

Column 6, line 50, after "143.1," delete --143--.

Column 6, line 52, after "faces" delete "144.7" and replace it with --144.1--.

Column 9, line 8, after "for" delete "movably" and replace it with --removably--.

Column 9, line 10, after "connecting" delete "mean" and replace it with --means--.

Column 9, line 41, after "a" delete "third" and replace it with --thread--.

Column 11, line 20, after "connecting" delete "mean" and replace it with --means--.

Signed and Sealed this

Twenty-third Day of March, 1993

*Attest:*

STEPHEN G. KUNIN

*Attesting Officer*  *Acting Commissioner of Patents and Trademarks*